(12) United States Patent
Stackelhouse

(10) Patent No.: US 7,295,126 B2
(45) Date of Patent: Nov. 13, 2007

(54) PERFORATED PLANE MOISTURE SENSOR

(75) Inventor: Scott D. Stackelhouse, Clearwater, FL (US)

(73) Assignee: Honeywell International Inc., Morristown, NJ (US)

( * ) Notice: Subject to any disclaimer, the term of this patent is extended or adjusted under 35 U.S.C. 154(b) by 248 days.

(21) Appl. No.: 11/029,429

(22) Filed: Jan. 5, 2005

(65) Prior Publication Data

US 2006/0145879 A1 Jul. 6, 2006

(51) Int. Cl.
*G08B 21/00* (2006.01)

(52) U.S. Cl. .............. 340/604; 340/602; 340/605; 340/618; 340/620; 338/35; 73/75

(58) Field of Classification Search .......... 340/604, 340/602, 603, 605, 618, 620; 73/73, 75; 338/34, 35, 286, 505; 361/286; 364/505
See application file for complete search history.

(56) References Cited

U.S. PATENT DOCUMENTS

| | | | |
|---|---|---|---|
| 4,386,336 A | 5/1983 | Kinomoto et al. | 338/35 |
| 4,571,543 A * | 2/1986 | Raymond et al. | 324/425 |
| 5,008,650 A * | 4/1991 | Hoiberg | 340/604 |
| 5,069,069 A | 12/1991 | Miyagishi et al. | 73/335 |
| 5,177,662 A | 1/1993 | Thoma | 361/286 |
| 5,315,291 A * | 5/1994 | Furr | 340/605 |
| 5,473,933 A | 12/1995 | Soga et al. | 73/29.2 |
| 5,748,092 A * | 5/1998 | Arsenault et al. | 340/604 |
| 5,767,687 A * | 6/1998 | Geist | 324/664 |
| 5,801,307 A * | 9/1998 | Netzer | 73/170.17 |
| 6,310,555 B1 * | 10/2001 | Stern | 340/605 |
| 6,647,782 B2 | 11/2003 | Toyoda | 73/335.04 |
| 6,724,612 B2 | 4/2004 | Davis et al. | 361/328 |

* cited by examiner

*Primary Examiner*—Hung Nguyen
(74) *Attorney, Agent, or Firm*—Kermit D. Lopez; Luis M. Ortiz; William B. Shelby

(57) ABSTRACT

A moisture sensing apparatus, system and method. In general, a surface can be provided, and one or more conductor pairs located in a plane of the surface. Each conductor of the conductor pair(s) is insulated from one another. Water droplets forming on the conductor pair(s) thereby provide a quantifiable measurement of water on the surface. A controller can be electrically connected to the conductor pair(s), wherein the controller provides data indicative of whether or not the conductor pair is shorted.

20 Claims, 2 Drawing Sheets

PERFORATED PLANE MOISTURE SENSOR

TECHNICAL FIELD

Embodiments are generally related to sensing devices and techniques. Embodiments are also related to moisture sensing devices and systems. Embodiments also relate to discrete components and circuits utilized in sensing applications.

BACKGROUND OF THE INVENTION

Moisture sensing devices are utilized in number of sensing applications. One type of a conventional moisture sensing device is a humidity sensor, which can provide for the measurement of relative humidity (RH) over wide RH ranges (e.g., 1%-100%), but which continues to be a challenge in design and construction. Moisture sensing devices can be implemented in the context of semiconductor-based sensors utilized in many industrial applications. Solid-state semiconductor devices are found in most electronic components today. Semiconductor-based sensors, for example, are fabricated using semiconductor processes.

Many modern manufacturing processes, for example, generally require measurement of moisture contents corresponding to dew points between −40° C. and 180° C., or a relative humidity between 1% and 100%. Such devices do not, however, adequately measure the amount of moisture collected on a particular surface, which is an important factor in maintaining the efficiency and safety of manufacturing facilities. There is thus a need for a durable, compact, efficient moisture detector that can be used effectively in these processes to measure very small moisture content on surfaces.

Moisture can be measured by a number of techniques. In a semiconductor-based system, for example, moisture can be measured based upon the reversible water absorption characteristics of polymeric materials. The absorption of water into a sensor structure causes a number of physical changes in the active polymer. These physical changes can be transduced into electrical signals which are related to the water concentration in the polymer and which in turn are related to the relative humidity in the air surrounding the polymer. Such devices, however, are limited in range and efficiency and do not adequately detect moisture on surfaces.

Two of the most common physical changes are the change in resistance and the change in dielectric constant, which can be respectively translated into a resistance change and a capacitance change. It has been found, however, that elements utilized as resistive components suffer from the disadvantage that there is an inherent dissipation effect caused by the dissipation of heat due to the current flow in the elements necessary to make a resistance measurement. The result is erroneous readings, among other problems.

It is therefore believed that a solution to some of the problems associated with conventional moisture sensing devices involves the design and implementation of discrete components and circuits, based on simple principles of electrical conducting circuits, which to date have not been fully implemented in moisture sensing applications.

BRIEF SUMMARY

The following summary is provided to facilitate an understanding of some of the innovative features unique to the embodiments disclosed herein and is not intended to be a full description. A full appreciation of the various aspects of the embodiments can be gained by taking the entire specification, claims, drawings, and abstract as a whole.

It is, therefore, one aspect of the present invention to provide improved sensor devices and sensing techniques.

It is another aspect of the present invention to provide for an improved moisture sensor.

It is also an aspect of the present invention to provide an apparatus and system for detecting moisture on a surface.

The aforementioned aspects of the invention and other objectives and advantages can now be achieved as described herein. A moisture sensing apparatus, system and method are disclosed herein. In general, a surface can be provided, and one or more conductor pairs located in a plane of the surface. Each conductor of the conductor pair(s) is insulated from one another. Water droplets forming on the conductor pair(s) allow for conduction between the insulated conductor pair(s) thereby providing a quantifiable measurement of water on the surface.

A controller can be electrically connected to the conductor pair(s), wherein the controller provides data indicative of whether or not the conductor pair is shorted. A microprocessor can also be provided for processing the data indicative of whether or not the conductor pair is shorted, such that the microprocessor communicates with the controller. The conductor pair comprises a first conductor concentrically located with a second conductor, such that at least one water droplet forms between the first and second conductors of the conductor pair.

DETAILED DESCRIPTION OF THE INVENTION

The particular values and configurations discussed in these non-limiting examples can be varied and are cited merely to illustrate at least one embodiment and are not intended to limit the scope thereof.

Figure 1:
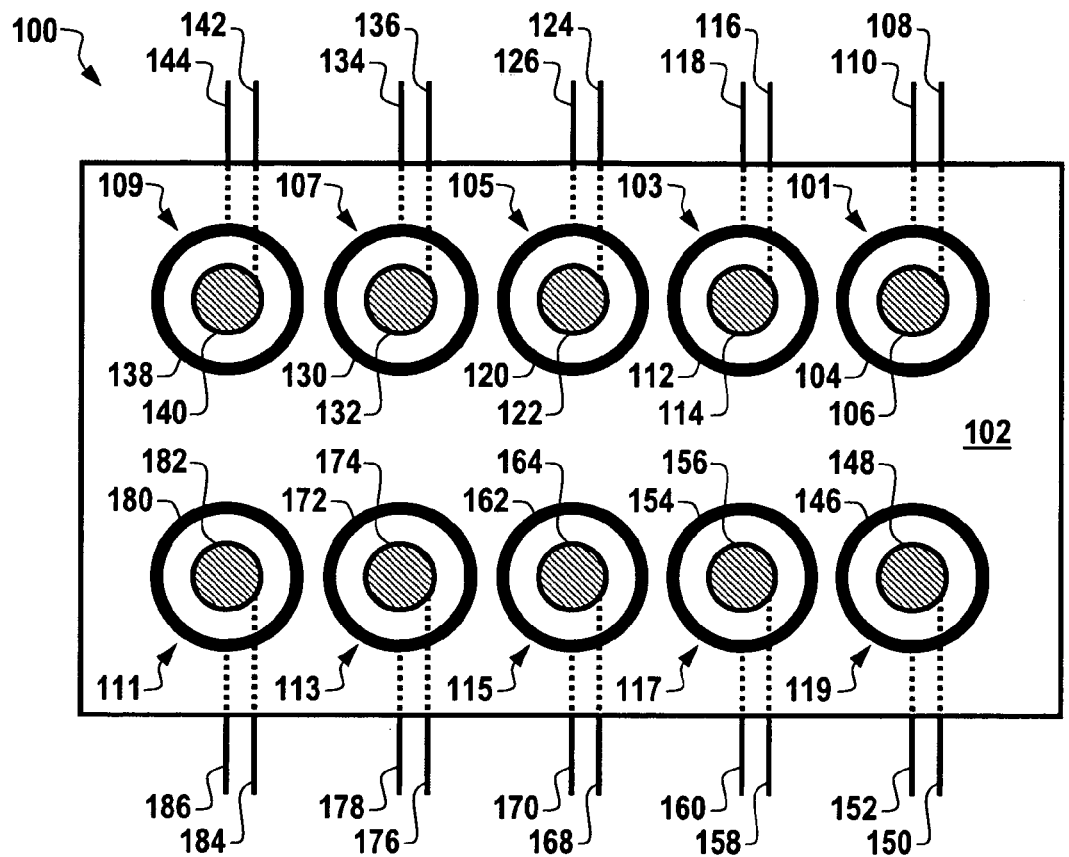
FIG. 1 illustrates a top view of a moisture sensing apparatus, which can be implemented in accordance with a preferred embodiment.

FIG. 1 illustrates a top view of a moisture sensing apparatus 100, which can be implemented in accordance with a preferred embodiment. The moisture sensing apparatus 100 generally includes a surface 102 and one or more conductor pairs 101, 103, 105, 107, 109, 111, 113, 115, 117, and 119 located in or on a plane of surface 102. Each of the conductor pairs 101, 103, 105, 107, 109, 111, 113, 115, 117, and 119 include concentric, but isolated conductors. Note that surface 102 can be configured as a surface of a substrate or other base material.

Thus, conductor pair 101 can be composed of a conductor 104 and a conductor 106. Conductor pair 103 generally includes a conductor 112 and 114. Similarly, conductor pair 105 comprises a conductor 120 and a conductor 122. Conductor pair 107 includes a conductor 130 and a conductor 132, while conductor pair 109 includes a conductor 138 and a conductor 140. Likewise, conductor pair 111 includes a conductor 180 and a conductor 182. Conductor pair 113 is composed of a conductor 172 and a conductor 174. Conductor pair 115 comprises a conductor 162 and a conductor 164.

Additionally, conductor pair 117 includes a conductor 154 and a conductor 156. Finally, conductor pair 117 includes a conductor a 146 and a conductor 148. Thus, each of the aforementioned conductor pairs are composed of two isolated conductors exposed as concentric rings at the surface 102 of sensing apparatus 100. Water droplets on the surface 102 of apparatus 100 create an electrical connection between the two conductors, thereby providing a quantifiable measurement of the water on the surface 102.

Each conductor can be connected to an electrical conducting wire or electrical connection. For example, conductor 104 can be connected to an electrical conducting wire 110, while conductor 106 can be coupled an electrical conducting wire 108. Similarly, conductor 112 can be connected to an electrical conducting wire 118, and conductor 114 can be coupled an electrical conducting wire 116. Likewise, conductor 120 is generally connected to an electrical conducting wire 126, while conductor 122 can be coupled to an electrical conducting wire 124. Conductor 130 is generally connected to an electrical conducting wire 136, and conductor 132 can be connected an electrical conducting wire 134.

Additionally, conductor 138 is generally connected to an electrical conducting wire 144, while conductor 140 can be connected an electrical conducting wire 142. Also, conductor 180 can be connected to an electrical conducting wire 184, while conductor 182 can be connected an electrical conducting wire 186. Conductor 172 is generally connected to an electrical conducting wire 176, while conductor 174 can be connected an electrical conducting wire 178. Similarly, conductor 162 can be connected to an electrical conducting wire 170, while conductor 164 can be connected an electrical conducting wire 168. Likewise, conductor 154 can be connected to an electrical conducting wire 158, while conductor 156 is generally connected an electrical conducting wire 160. Finally, conductor 146 is generally connected to an electrical conducting wire 150, while conductor 148 can be connected an electrical conducting wire 152.

Figure 2:
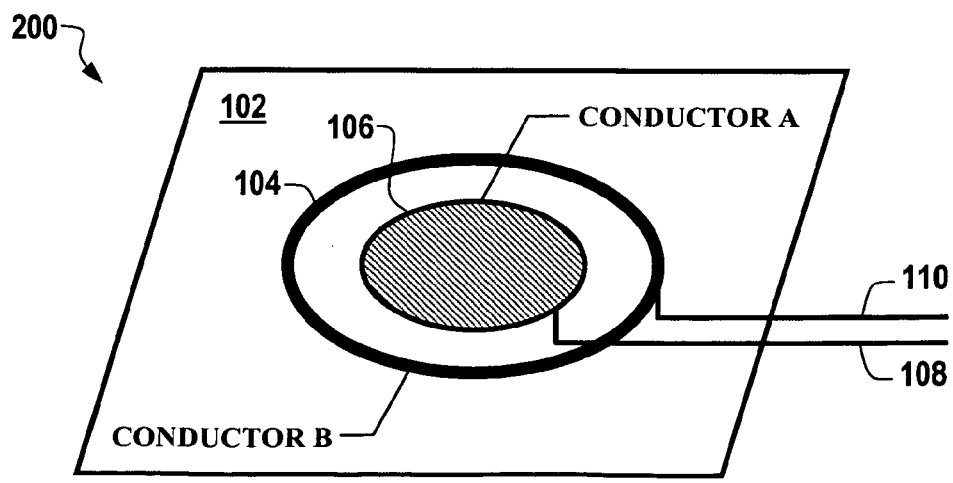
FIG. 2 illustrates a perspective view of the surface of the moisture sensing apparatus depicted in FIG. 1.

FIG. 2 illustrates a perspective view of the surface 102 of the moisture sensing apparatus 100 depicted in FIG. 1. Note that in FIGS. 1-2, identical or similar are parts are generally indicated by identical reference numerals. FIG. 2 therefore provides a detailed view of a portion of apparatus 100 illustrated in FIG. 1. It can be appreciated that water droplets can form close to the circuit formed between conductor 104 and conductor 106 on surface 102. Conductor 104 is isolated from conductor 106 and together the two conductors 104, 106 form a concentric ring configuration, which can be electrically connected to via wires 110, 108 to a control circuit (not shown in FIG. 3), which can be utilized to determine if the pair of conductors 104, 106 has or has not been shortened.

Figure 3:
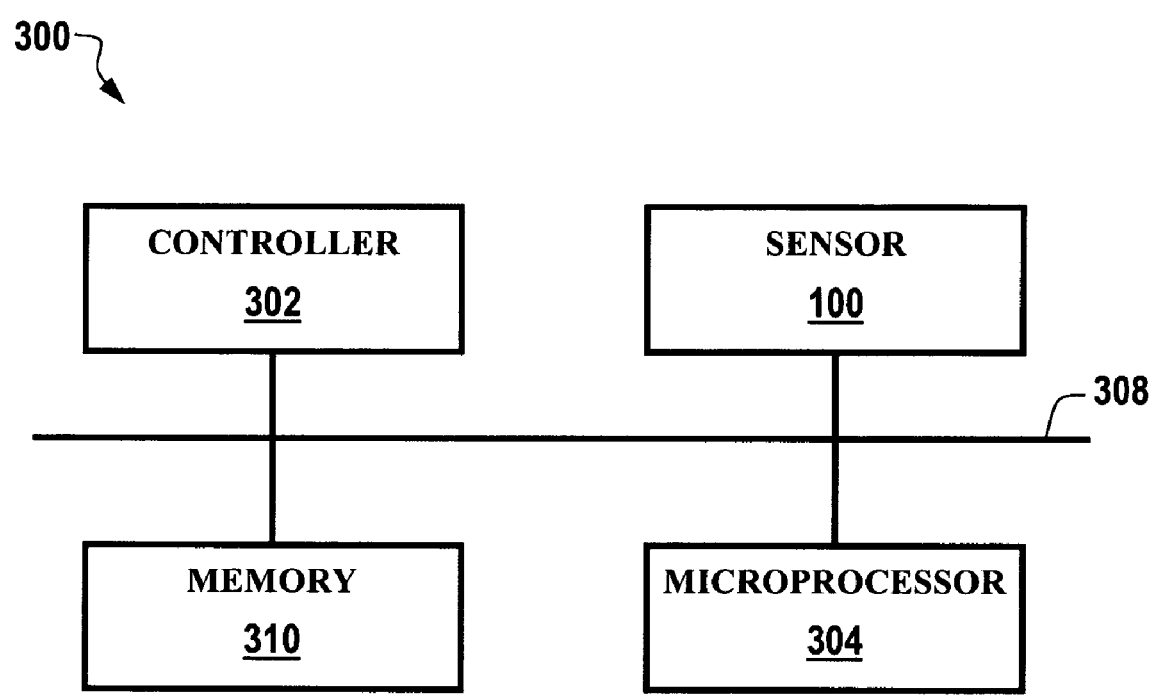
FIG. 3 illustrates a block diagram of a moisture sensing system, which can be implemented in accordance with an alternative embodiment.

FIG. 3 illustrates a block diagram of a moisture sensing system 300, which can be implemented in accordance with an alternative embodiment. Note that in FIGS. 1-3, identical or similar are parts are generally indicated by identical reference numerals. System 300 generally provides a means of moisture detection by way of electrical conduction. The water droplets close to discrete circuits can provide a quantifiable feedback regarding the moisture level on surface 102. Thus, system 300 includes the sensing apparatus 100 depicted in FIG. 1. System 300 also includes a controller 302 and a microprocessor 304, which can be electrically connected via a system bus 308 to sensing apparatus 100.

System 300 can further include a memory 310 in which data can be stored and then retrieved. Controller 302 can be implemented as a computer chip that controls the transfer of data between the microprocessor 304 and memory 310 or between the microprocessor 304 and other devices, such as, sensing apparatus 100. Microprocessor 304 can be implemented as a computational and control unit (in association with controller 302) in order to interpret and execute instructions, particularly moisture sensing instructions. Microprocessor 304 can therefore be configured to fetch, decode, and/or execute instructions and to transfer information to and from other resources (e.g., sensing apparatus 100) over the communication path, i.e., bus 308.

System 300 can be utilize in a number of moisture sensing applications. For example, system 300 can be applied to manufacturing operations, such as in the fabrication of semiconductor products. Other possible applications also include commercial and consumer implementations, such as in aerospace facilities or in association with automobiles for detecting moisture thereof. Another application includes agricultural settings where the need to detect moisture is or paramount concern, particularly in dry climates.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A moisture sensing apparatus, comprising:
a surface; and
a plurality of conductor pairs located in a plane of said surface, wherein both conductors of each conductor pair of said plurality of conductor pairs is insulated from one another, wherein water droplets forming on said surface create an electrical connection between both conductors of at least one conductor pair of said plurality of conductor pairs, thereby providing a quantifiable measurement of water on said surface.

2. The apparatus of claim 1 further comprising:
a controller electrically connected to said plurality of conductor pairs, wherein said controller provides data indicative of whether or not said at least one conductor pair is shorted.

3. The apparatus of claim 2 further comprising:
a microprocessor for processing said data indicative of whether or not said at least one conductor pair is shorted, wherein said microprocessor communicates with said controller.

4. The apparatus of claim 1 wherein said each conductor pair comprises a first conductor co-centrically located with a second conductor, such that at least one water droplet forms between said first and second conductors of said at least one conductor pair.

5. The apparatus of claim 4 wherein said each conductor pair comprises co-centrically shaped rings.

6. The apparatus of claim 5 wherein said surface comprises a surface of a sensor.

7. The apparatus of claim 1 wherein said surface comprises a substrate.

8. The apparatus of claim 1 wherein said quantifiable measurement of water on said surface comprises feedback data indicative of the moisture level of said surface.

9. A moisture sensing system, comprising:
   a surface;
   a plurality of conductor pairs located in a plane of said surface, wherein both conductors of each conductor pair of said plurality of conductor pairs is insulated from one another;
   a controller electrically connected to said plurality of conductor pairs, wherein said controller provides data indicative of whether or not at least one conductor pair of said plurality of conductor pairs is shorted;
   a microprocessor for processing said data indicative of whether or not said at least one conductor pair is shorted, wherein said microprocessor communicates with said controller, wherein water droplets forming on said surface create an electrical connection between both conductors of said at least one conductor pair, thereby providing a quantifiable measurement of water on said surface.

10. The system of claim 9 wherein said each conductor pair comprises a first conductor co-centrically located with a second conductor, such that at least one water droplet forms between said first and second conductors of said at least one conductor pair.

11. The system of claim 10 wherein said each conductor pair comprises a plurality of co-centrically shaped rings.

12. The system of claim 11 wherein said surface comprises a surface of a sensor.

13. The system of claim 9 wherein said surface comprises a substrate.

14. The system of claim 9 wherein said quantifiable measurement of water on said surface comprises feedback data indicative of the moisture level of said surface.

15. A moisture sensing method, comprising the steps of:
    providing a surface; and
    locating a plurality of conductor pairs in a plane of said surface, wherein both conductors of each conductor pair of said plurality of conductor pairs is insulated from one another, wherein water droplets forming on said surface create an electrical connection between both conductors of at least one conductor pair, thereby providing a quantifiable measurement of water on said surface.

16. The method of claim 15 further comprising the step of:
    electrically connecting a controller to said plurality of conductor pairs, wherein said controller provides data indicative of whether or not said at least one conductor pair is shorted.

17. The method of claim 16 further comprising the step of:
    providing a microprocessor for processing said data indicative of whether or not said at least one conductor pair is shorted, wherein said microprocessor communicates with said controller.

18. The method of claim 15 further comprising the step of:
    configuring said each conductor pair to comprise a first conductor co-centrically located with a second conductor, such that at least one water droplet forms between said first and second conductors of said at least one conductor pair.

19. The method of claim 15 wherein said each conductor pair comprises co-centrically shaped rings.

20. The method of claim 19 wherein said surface comprises a surface of a sensor.

* * * * *